US006677472B2

(12) United States Patent
Shirai et al.
(10) Patent No.: US 6,677,472 B2
(45) Date of Patent: Jan. 13, 2004

(54) BIS (ARYLSULFONYLAMINO CARBONYLAMINOBENZOATE) COMPOUNDS AND THERMOSENSITIVE RECORDING MATERIALS CONTAINING SAME

(75) Inventors: Ayako Shirai, Yokohama (JP); Yoshiyuki Takahashi, Tokyo (JP)

(73) Assignee: Oji Paper Co., Ltd., Tokyo (JP)

(*) Notice: Subject to any disclaimer, the term of this patent is extended or adjusted under 35 U.S.C. 154(b) by 223 days.

(21) Appl. No.: 09/994,626

(22) Filed: Nov. 28, 2001

(65) Prior Publication Data

US 2002/0065196 A1 May 30, 2002

Related U.S. Application Data

(62) Division of application No. 09/548,287, filed on Apr. 12, 2000, now Pat. No. 6,486,094.

(30) Foreign Application Priority Data

Apr. 13, 1999 (JP) ........................................ 11-105293
Feb. 21, 2000 (JP) .................................... 2000-042986

(51) Int. Cl.[7] .......................................... C07C 311/00
(52) U.S. Cl. ................................................ 560/12
(58) Field of Search ....................................... 560/12

(56) References Cited

U.S. PATENT DOCUMENTS 5,256,618 A 10/1993 Takahashi et al.

FOREIGN PATENT DOCUMENTS

| | | |
|---|---|---|
| EP | 0 535 887 A | 4/1993 |
| EP | 0 633 145 A | 1/1995 |
| JP | B-43-4160 | 2/1968 |
| JP | B-45-14039 | 5/1970 |
| JP | B-48-27736 | 8/1973 |
| JP | 56146796 | 11/1981 |
| JP | 58199189 | 11/1983 |
| JP | 59093387 | 5/1984 |
| JP | 59114096 | 6/1984 |
| JP | 59167292 | 9/1984 |
| JP | 60078782 | 5/1985 |
| JP | A-62-19485 | 1/1987 |
| JP | 62164579 | 7/1987 |
| JP | 62169681 | 7/1987 |
| JP | 07-257033 A2 * | 10/1994 |

* cited by examiner

*Primary Examiner*—Johann Richter
*Assistant Examiner*—Paul A. Zucker
(74) *Attorney, Agent, or Firm*—Arent Fox Kintner Plotkin Kahn

(57) ABSTRACT

A thermosensitive recording material having high whiteness and resistance to color formation under high temperature, high humidity conditions has a thermosensitive colored image-forming layer formed on a substrate sheet and includes a dye precursor, a binder and a color developing agent including a compound of the formula (I) and optionally a compound of the formula (V).

(I)

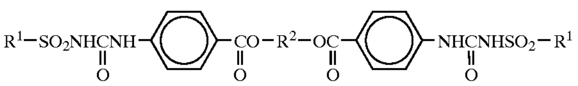

(V)

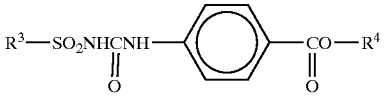

$R^1$, $R^3$=unsubstituted or methyl or chlorine-substituted aryl group, $R^2$=at least $C_3$ divalent organic group, $R^4$=at least $C_3$ alkyl, aralkyl or aryloxyalkyl group.

3 Claims, No Drawings

BIS (ARYLSULFONYLAMINO CARBONYLAMINOBENZOATE) COMPOUNDS AND THERMOSENSITIVE RECORDING MATERIALS CONTAINING SAME

This application is a divisional of Ser. No. 09/548,287 filed Apr. 12, 2000 now U.S. Pat. No. 6,486,094.

BACKGROUND OF THE INVENTION (1) Field of the Invention

The present invention relates to novel bis (arylsulfonylaminocarbonylaminobenzoate) compounds and to thermosensitive recording materials containing the same for forming colored images upon heating. More particularly, the present invention relates to novel bis (arylsulfonylaminocarbonylaminobenzoate) compounds and thermosensitive recording materials containing the same and having a high whiteness, an excellent colored image-retaining stability, due to which the color-developed images are not erased, and a high recording sensitivity.

The thermosensitive recording materials of the present invention contains the above-mentioned specific compounds as color-developing components, exhibit a high recording sensitivity and a high whiteness, can record thereon colored images having a good storage property over a long time, and have a high environmental resistance such as a high humidity resistance, a high oil resistance and a high plasticizer-resistance. Thus the thermosensitive recording materials of the present invention are usable for image-recording sheets, cash-dispenser sheets, ticket cards, commuting ticket cards, labels, for example, POS labels, cards, for example, prepaid cards, and pass cards.

(2) Description of the Related Art

Generally, a thermosensitive recording material comprises a substrate comprising a paper sheet, a synthetic paper sheet or a plastic film and a thermosensitive colored image-forming layer formed on the substrate and comprising, as principal components, a color-forming component, for example, an electron-donative leuco dye and a color-developing component comprising an organic acid substance, for example, an electron-acceptive phenol compound. The above-mentioned two components react with each other upon heating to form colored images. This type of thermosensitive recording material is disclosed in Japanese Examined Patent Publication No. 43-4,160, No. 45-14,039 and No. 48-27,736, and is employed in practice.

The thermosensitive recording material is compact, cheap and is easy to maintain, and thus is used in a broad range of practical applications, for example, outputs of computers, facsimiles, automatic ticket vending machines, printers for scientific and measurement equipments, printer for CRT medical measurements and the like. However, in the conventional thermosensitive recording materials, in which a thermosensitive colored image-forming layer contains a color-forming dye component, a color-developing component and a binder, the color-forming reaction is reversible and thus it is known that the colored images is erased with the lapse of time. The color-erasure is accelerated when the images are exposed to light, a high humidity atmosphere or a high temperature atmosphere. The color-erasure is further promoted by immersing in water for long period or by contacting with an oil, for example, salad oil, or with a plasticizer, to such an extent that the images cannot be read or noted.

Regarding the thermosensitive colored image-forming layer using a color-forming system containing a dye precursor including, as a principal component, a colorless or light colored lactone cyclic compound, many attempts to control the color-erasing phenomenon have been made. For example, in one attempt, a phenol compound-containing antioxidant is contained in the thermosensitive colored image-forming layer, as disclosed in Japanese Unexamined Patent Publication No. 60-78,782, No. 59-167,292, No. 59-114,096 and No. 59-93,387; in another attempt, a protective layer is formed from a hydrophobic polymer emulsion on the thermosensitive colored image-forming layer, as disclosed in Japanese Unexamined Patent Publication No. 56-146,796; in still another attempt, the thermosensitive colored image-forming layer is coated with an intermediate layer formed from an emulsion of a water-soluble polymeric compound or a hydrophobic polymeric compound, and the intermediate layer is coated by a surface layer formed from a oily lacquer containing, as a resin component, a hydrophobic polymeric compound, as disclosed in Japanese Unexamined Patent Publication No. 58-199,189; in still another attempt, a phenol compound-containing color developing agent is employed in combination with an epoxy compound, as disclosed in Japanese Unexamined Patent Publication No. 62-164,579; and in further another attempt, a metal salt of a specific salicylic acid derivative is employed as a color-developing agent, as disclosed in Japanese Unexamined Patent Publication No. 62-169,681.

It has been found that the anti-oxidative phenol compound contained in the thermosensitive colored image-forming layer does not contribute to improving the oil resistance of the resultant colored images (a retention of the color density of the colored images a fixed time after a salad oil is brought into contact with the colored images) and the plasticizer resistance of the resultant colored images (a retention of the color density of the colored images a fixed time after a plasticizer is brought into contact with the colored images), in comparison with those on the comparative thermosensitive colored image-forming layer containing no anti-oxidative phenol compound.

Also, in the thermosensitive recording material having the protective layer or the surface layer as mentioned above, the erasure of the colored images due to contact with the oil or plasticizer for a short time can be restricted, but the erasure of the colored images due to the contact with the oil or plasticizer over a long period cannot be prevented, and thus the protective layer and the surface layer are not recognized as essential means for solving the above-mentioned problems.

Further, when the phenol compound is employed in combination with the epoxy compound, a time necessary to stabilize the colored images formed by applying a heating procedure imagewise to the resultant thermosensitive colored image-forming layer, is relatively long. Thus when a salad oil or a plasticizer is brought into contact with the colored images immediately after the colored images are formed on the colored image-forming layer, the colored images are erased to a certain extent.

When the metal salt of the specific salicylic acid derivative is used for the thermosensitive recording material, the retention of the colored images can be improved, but a heat resistance test applied to the thermosensitive recording material causes the non-recorded white portions of the recording material to be colored. Also, the specific salicylic acid derivative is disadvantageous in that the chemical structure of the derivative is complicated and thus the derivative is too expensive.

Generally, to enhance the storage stability of the thermosensitive recording material, a specific additive or a special color-forming material must be used, and thus the resultant colored image-forming layer generally exhibits a relatively low thermosensitivity.

Japanese Unexamined Patent Publication No. 62-19,485 discloses specific color-developing compounds having a sulfonylamide group. The resultant thermosensitive recording material exhibits, however, a color-forming performance the same as or lower than that of the conventional thermosensitive recording material containing the conventional color-developing phenol compound. Namely, the specific color-developing compounds failed to provide an excellent color-forming performance.

SUMMARY OF THE INVENTION

An object of the present invention is to provide a thermosensitive recording material having a high whiteness, a satisfactory resistance of non-recorded portions thereof to unwilling color-development in hot environment, an excellent storage stability including high resistances to oils and plasticizers over a long period, and a high thermosensitivity for color-formation, and new color-developing compounds useful for the thermosensitive recording material.

Another object of the present invention is to provide a thermosensitive recording material not only useful for thermosensitive recording traveller's tickets for ticket-vending machines, coupon ticket cards and commuter's ticket cards which must have a high storage stability, labels for barcode system for POS which labels are adhered to a surfaces of packages of foods packed with polyvinyl chloride films and are most likely brought into contact with oils or plasticizers, but also useful as recording sheets of facsimile machines and word processor machines which sheets must have a high sensitivity for recording and a high storage stability, and recording sheets for image printers for CRTs, and new bis(arylsulfonylaminocarbonylaminobenzoate) compounds to be contained as color-developing agents in the recording material.

The above-mentioned objects can be attained by the thermosensitive recording material of the present invention and the new bis(arylsulfonylaminocarbonylaminobenzoate) compounds of the present invention.

The thermosensitive recording material of the present invention comprises substrate sheet and a thermosensitive colored image-forming layer formed on at least one surface of the substrate sheet and comprising at least one colorless or light-colored dye precursor, a color-developing agent reactive with the dye precursor upon heating to thereby develop a color, and a binder, wherein the color developing agent comprises at least one compound of the formula (I):

(I)

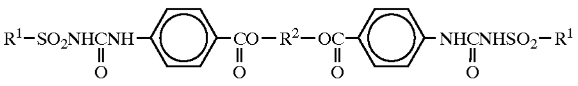

wherein $R^1$ represents a member selected from the group consisting of unsubstituted aryl groups and substituted aryl groups with at least one substituent selected from the group consisting of a methyl group and a chlorine atom, and $R^2$ represents a divalent organic group having 3 or more carbon atoms.

In the thermosensitive recording material of the present invention, the divalent organic group represented by $R^2$ in the formula (I) is preferably selected from the group consisting of:

$-(CH_2)_m-$ groups, and $-(CH_2CH_2O)_n-CH_2CH_2-$ groups wherein m represents an integer of 3 to 30, and n represents an integer of 1 to 20.

In the thermosensitive recording material of the present invention, the color-developing compound of the formula (I) is preferably selected from the compounds of the formulae (II), (III) and (IV):

(II)

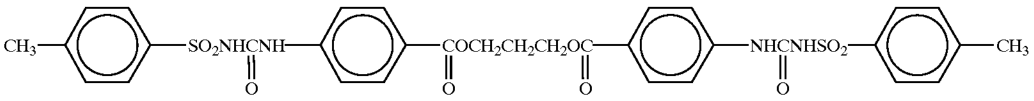

(III)

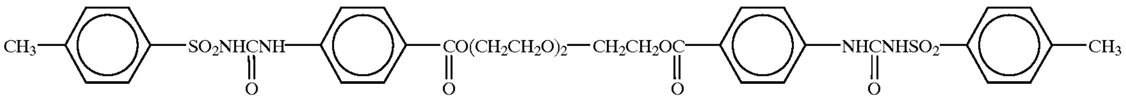

and (IV)

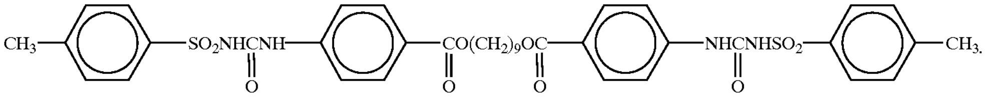

In the thermosensitive recording material of the present invention, the color-developing agent optionally further comprises, in addition to the compound of the formula (I), at least one compound of the formula (V):

(V)

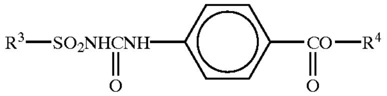

wherein $R^3$ represents a member selected from the group consisting of unsubstituted aryl groups and substituted aryl groups with at least one substituent selected from the group consisting of a methyl group and a chlorine atom, and $R^4$ represents a member selected from the group consisting of alkyl groups having 3 or more carbon atoms, aralkyl groups and aryloxyalkyl groups.

In the thermosensitive recording material of the present invention, the compound of the formula (V) is preferably that of the formula (VI):

(VI)

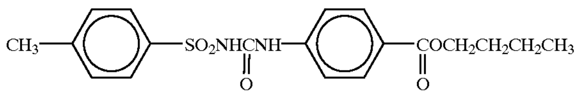

The bis(arylsulfonylaminocarbonylaminobenzoate) compound of the present invention is of the formula (I):

(I)

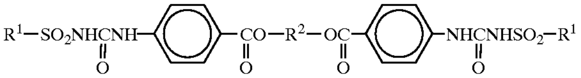

wherein $R^1$ represents a member selected from the group consisting of unsubstituted aryl groups and substituted aryl groups with at least one substituent selected from the group consisting of a methyl group and a chlorine atom, and $R^2$ represents a divalent organic group having 3 or more carbon atoms.

In the bis(arylsulfonylaminocarbonylaminobenzoate) compound of the formula (I) of the present invention, the divalent organic group represented by $R^2$ is preferably selected from the group consisting of a $-(CH_2)_m-$ group and a $-(CH_2CH_2O)_n-CH_2CH_2-$ group wherein m represents an integer of 3 to 30 and n represents an integer of 1 to 20.

The bis(arylsulfonylaminocarbonylaminobenzoate) compound of the present invention is preferably selected from the group consisting of:

1,3-trimethylene bis(4-(p-toluenesulfonylaminocarbonylamino)benzoate) of the formula (II):

(II)

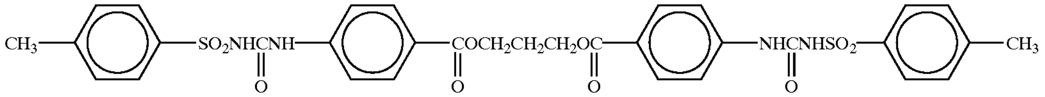

1,8-(3,6-dioxaoctylene)bis(4-(p-toluenesulfonylaminocarbonylamino)benzoate) of the formula (III):

(III)

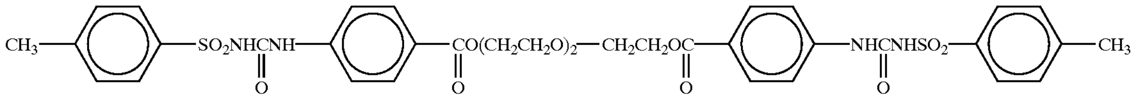

and 1.9-nonamethylene bis(4-(p-toluenesulfonylaminocarbonylamino)benzoate) of the formula (IV):

(IV)

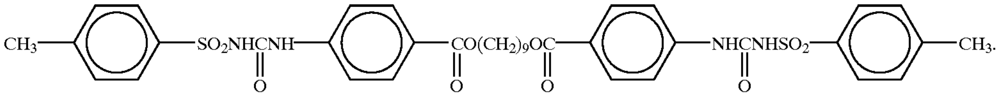

DESCRIPTION OF THE PREFERRED EMBODIMENTS

The compound of the formula (I) and the optional compound of the formula (V) used in the thermosensitive colored image-forming layer of the present invention serve as color-developing agents. Namely, although the compounds of the formula (I) and the formula (V) have no acid functional group, for example, phenolic hydroxyl group and carboxyl group, they exhibit a strong color-developing property to basic leuco dye. The strong color-developing property is assumed to be due to a phenomenon in which the urea groups in the compounds of the formulae (I) and (V) are activated by the sulphonyl group located adjacent to the urea group.

The compounds represented by the general formula (I) are novel compounds. In the formula (I), the group represented by $R^1$ is selected from the group consisting of unsubstituted aryl groups and substituted aryl groups with at least one substituent selected from the group consisting of a methyl group and a chlorine atom. Particularly, $R^1$ is preferably selected from a phenyl group, a 2-naphthyl group, a p-tolyl group, an o-tolyl group, a m-tolyl group and a p-chlorophenyl group.

In the formula (I), the group represented by $R^2$ is not specifically limited to specific groups, as long as the $R^2$ group is a divalent organic group having 3 or more carbon atoms. Preferably, the group represented by $R^2$ is a member selected from the following group.

(a) Divalent aliphatic or cycloaliphatic hydrocarbon groups having chemical structures corresponding to those of aliphatic or cycloaliphatic hydrocarbons from each of which structures two hydrogen atoms are excluded, particularly $-(CH_2)_m-$ groups in which m represents an integer of 3 to 30.

Preferably, the group (a) includes trimethylene, tetramethylene, pentamethylene, hexamethylene and nonamethylene groups, and substituted or branched or cyclic divalent hydrocarbon groups, for example, 1-methyl-1,3-trimethylene, 2,3-dimethyl-1,4-tetramethylene, 1,4-cyclohexylene, 1,4-cyclohexane dimethylene groups.

(b) Divalent hetero-aliphatic or cycloaliphatic hydrocarbon groups having chemical structures corresponding to those of hetero-aliphatic and cycloaliphatic hydrocarbons from each of which structures two hydrogen atoms are excluded, particularly $-(CH_2CH_2O)_n-CH_2CH_2-$ group wherein n represents an integer of 1 to 20.

Preferably, the group (b) includes 1,5-(3-oxapentylene), 1,5-(3-thiopentylene), 2,5-(1-oxacyclohexylene), 1-oxacyclohexane-2,5-dimethylene, 1,8-(3,6-dioxaoctylene) and 1,12-(3,6,9-trioxadodecylene) groups.

(c) Divalent alkyl- or heteroalkyl-substituted aryl groups having chemical structure corresponding to those of alkyl-substituted aryl compounds or heteroalkyl-substituted aryl compounds, in each of which structures, two hydrogen atoms are excluded, from the alkyl group or the hetero atom-substituted group.

Preferably, the group (c) include an α,α'-(p-xylylene) group, an α,α'-(m-xylylene) group, a β,β'-(1,4-di (dimethylene)benzene) group, a γ,γ'(1,4-di (trimethylene)benzene) group and a β,β'-hydrogen atoms-excluded p-hydroquinone-diethylether group.

Examples of the compound of the formula (I) usable as a color developing agent of the present invention are shown below.

1,3-trimethylene bis(4-(p-toluenesulfonylaminocarbonylamino)benzoate), 1,3-trimethylene bis(4-(o-toluenesulfonylaminocarbonylamino)benzoate), 1,3-trimethylene bis(4-(m-toluenesulfonylaminocarbonylamino)benzoate), 1,4-tetramethylene bis(4-(p-toluenesulfonylaminocarbonylamino)benzoate), 1,4-tetramethylene bis(4-(o-toluenesulfonylaminocarbonylamino)benzoate), 1,4-tetramethylene bis(4-(m-toluenesulfonylaminocarbonylamino)benzoate), propylene bis(4-(p-toluenesulfonylaminocarbonylamino) benzoate), propylene bis(4-(o-toluenesulfonylaminocarbonylamino) benzoate), propylene bis(4-(m-toluenesulfonylaminocarbonylamino) benzoate), 1,5-(3-oxapentylene) bis(4-(p-toluenesulfonylaminocarbonylamino)benzoate), 1,5-(3-oxapentylene) bis(4-(m-toluenesulfonylaminocarbonylamino)benzoate, 1,8-(3,6-dioxaoctylene) bis(4-(p-toluenesulfonylaminocarbonylamino)benzoate), 1,12-(3,6,9-trioxadodecylene) bis(4-(p-toluenesulfonylaminocarbonylamino)benzoate), 1,9-nonamethylene bis(4-(p-toluenesulfonylaminocarbonylamino)benzoate), α,α'-(1,4-cyclohexanedimethylene) bis(4-(p-toluenesulfonylaminocarbonylamino)benzoate, α,α'-(1,4-cyclohexanedimethylene) bis(4-(o-toluenesulfonylaminocarbonylamino)benzoate), α,α'-(p-xylylene) bis(4-(p-toluene sulfonylaminocarbonylamino)benzoate), α,α'-(p-xylylene) bis(4-(m-toluenesulfonylaminocarbonylamino)benzoate).

These compounds of the formula (I) may be employed alone or in a combination of two or more thereof.

The bis(arylsulfonylaminocarbonylamino benzoate) compounds of the formula (I) are novel compounds. Also, 1,3-trimethylene bis(4-p-toluenesulfonylaminocarbonylamino)benzoate) of the formula (II), 1,8-(3,6-dioxaoctylene) bis(4-(p-toluenesulfonylaminocarbonylamino)benzoate) of the formula (III) and 1,9-nonamethylene bis(4-(p-toluene sulfonylaminocarbonylamino)benzoate) of the formula (IV) are novel compounds useful as color developing agents, of the thermosensitive recording material of the present invention.

In the color-developing agent for the thermosensitive colored image-forming layer of the present invention, at least one compound represented by the general formula (V) is optionally contained in addition to the compound of the formula (I). In the formula (V), $R^3$ represents a member selected from the group consisting of unsubstituted aryl groups and substituted aryl groups with at least one substituent selected from the group consisting of a methyl group and a chlorine atom. Preferably, the $R^3$ group is selected from phenyl, z-naphthyl, p-tolyl, o-tolyl, m-tolyl and p-chlorophenyl groups.

Also, in the formula (V), $R^4$ represents a member selected from the group consisting of alkyl groups having 3 or more carbon atoms, aralkyl groups and aryloxyalkyl groups. The alkyl group for $R^4$ is preferably selected from n-propyl, isopropyl, n-butyl, isobutyl, hexyl, cyclohexyl and octyl groups. The alkyl group for $R^4$ preferably has 3 to 8 carbon atoms. When the alkyl group represented by $R^4$ has 2 or less carbon atoms, the resultant color-developing compound exhibits a high melting temperature and thus the resultant thermosensitive recording material containing the compound having the high melting temperature may exhibit an unsatisfactory sensitivity. When the alkyl group for $R^4$ has more than 8 carbon atoms, the resultant compound may exhibit an unsatisfactory dispersing property. The aralkyl group represented by $R^4$ is preferably selected from benzyl, phenethyl, 2-naphthylmethyl, and 2-naphthylethyl groups. Further, $R^4$ may represent an aryloxyalkyl group in which an alkyl moiety is connected to an aryl moiety through an oxygen atom, for example, a phenoxyethyl or 2-naphthoxyethyl group.

Preferably, the color developing compound of the formula (V) is selected from propyl 4-(p-toluenesulfonylaminocarbonylamino)benzoate,
propyl 4-(m-toluenesulfonylaminocarbonylamino)benzoate,
propyl 4-(o-toluenesulfonylaminocarbonylamino)benzoate,
propyl 4-(benzenesulfonylaminocarbonylamino)benzoate,
propyl 4-(p-chlorobenzenesulfonylaminocarbonylamino) benzoate,
propyl 4-(m-chlorobenzenesulfonylaminocarbonylamino) benzoate,
butyl 4-(p-toluenesulfonylaminocarbonylamino)benzoate,
butyl 4-(o-toluenesulfonylaminocarbonylamino)benzoate,
butyl 4-(m-toluenesulfonylaminocarbonylamino)benzoate,
benzyl 4-(p-toluenesulfonylaminocarbonylamino)benzoate,
benzyl 4-(m-toluenesulfonylaminocarbonylamino)benzoate,
cyclohexyl 4-(p-toluenesulfonylaminocarbonylamino) benzoate,
butyl 4-(p-chlorobenzenesulfonylaminocarbonylamino) benzoate, and
butyl 4-(o-chlorobenzenesulfonylaminocarbonylamino) benzoate.

These compounds of the formula (V) may be employed alone or in a combination of two or more thereof.

In the thermosensitive colored image-forming layer of the present invention, the leuco dyes usable as dye-precursors may be selected from conventional leuco dyes, for example, triphenylmethane dyes, fluoran dyes, and diphenylmethane dyes. Preferably, the dye precursor comprises at least one member selected from 3-(4-diethylamino-2-ethoxyphenyl)-3-(1-ethyl-2-methylindole-3-yl)-4-azaphthalide,
crystal violet lactone,
3-(N-ethyl-N-isopentylamino)-6-methyl-7-anilinofluoran,
3-diethylamino-6-methyl-7-anilinofluoran,
3-diethylamino-6-methyl-7-(o- or p-dimethylanilino) fluoran,
3-(N-ethyl-N-p-toluidino)-6-(methyl-7-anilino)fluoran,
3-pyrrolidino-6-methyl-7-anilino-fluoran,
3-dibutylamino-6-methyl-7-anilino-fluoran,
3-(N-cyclohexyl-N-methylamino)-6-methyl-7-anilinofluoran,
3-diethylamino-7-(o-chloroanilino)fluoran,
3-diethylamino-7-(o-chloroanilino)fluoran,
3-dibutylamino-7-(m-trifluoromethylanilino)fluoran,
3-diethylamino-6-methyl-7-chlorofluoran,
3-diethylamino-6-methylfluoran,
3-cyclohexylamino-6-chlorofluoran,
3-(N-ethyl-N-hexylamino)-6-methyl-7-(p-chloroanilino) fluoran.

In the thermosensitive recording material of the present invention, unless the target effect of the present invention is damaged, a conventional color-developing compound may be employed in addition to the compound of the formula (I).

The additional color-developing compound may be selected from conventional color-developing phenolic compounds, compounds having only one sulfonylurea group per molecule thereof, and organic acids. The conventional color developing compounds are preferably selected from, for example, 2,2-bis(4-hydroxyphenyl)propane, namely bisphenol A, 1,1-bis(4-hydroxyphenyl)-1-phenylethane, 1,4-bis(1-methyl-1-(4'-hydroxyphenyl)ethyl)benzene, 1,3-bis(1-methyl-1-(4'-hydroxyphenyl)ethyl)benzene, dihydroxydiphenylethers (disclosed in Japanese Unexamined Patent Publication No. 1-180,382), benzyl p-hydroxybenzoate (disclosed in Japanese Unexamined Patent Publication No. 52-140,483), bisphenol S, 4-hydroxy-4'-isopropyloxydiphenylsulfone (disclosed in Japanese Unexamined Patent Publication No. 60-13,852), 1,1-di(4-hydroxyphenyl)cyclohexane, 1,7-di(4-hydroxyphenylthio)-3,5-dioxaheptane (disclosed in Japanese Unexamined Patent Publication No. 59-52,694), 3,3-diallyl-4,4'-dihydroxydiphenylsulfone (disclosed in Japanese Unexamined Patent Publication No. 60-208,286) and 2,4-bis(phenylsulfonyl)phenol (Japanese Unexamined Patent Publication No. 8-269,000).

In the thermosensitive recording material of the present invention, unless the target effect of the present invention is damaged, conventional thermo-fusible compounds may be contained, as a sensitizing agent, in the thermosensitive colored image-forming layer.

The typical fusible compounds are phenyl 1-hydroxy-2-naphthoate (Japanese Unexamined Patent Publication No. 57-191,089), p-benzylbiphenyl (Japanese Unexamined Patent Publication No. 60-82,382), benzylnaphthylether (Japanese Unexamined Patent Publication No. 58-87,094), dibenzyl terephthalate (Japanese Unexamined Patent Publication No. 58-98,285), benzyl p-benzyloxybenzoate (Japanese Unexamined Patent Publication No. 57-201,691), diphenyl carbonate and ditolyl carbonate (Japanese Unexamined Patent Publication No. 58-136,489), m-terphenyl (Japanese Unexamined Patent Publication No. 57-89,994), 1,2-bis(m-tolyloxy)ethane (Japanese Unexamined Patent Publication No. 60-56,588), 1,5-bis(p-methoxyphenoxy)-3-oxapentane (Japanese Unexamined Patent Publication No. 62-181,183), diesters of oxalic acid (Japanese Unexamined Patent Publication No. 64-1,583), and 1,4-bis(p-tolyloxy) benzene (Japanese Unexamined Patent Publication No. 2-153,783).

The thermosensitive colored image-forming layer of the thermosensitive recording material of the present invention optionally further contains waxes and preferably contains organic and inorganic pigments. The colored image-forming layer contains a binder for binding the components as mentioned above to the substrate.

In the thermosensitive colored image-forming layer, preferably, the color-forming leuco dye (dye precursor) is contained in a content of 5 to 20% by weight based on the total dry weight of the colored image-forming layer, and the color-developing agent including the compound of the formula (I) and optionally the compound of the formula (V) is contained in a content of 5 to 50% by weight based on the total dry weight of the colored image-forming layer. When the content of the color developing agent is less than 5% by weight, the color developing performance of the resultant colored image-forming layer may be insufficient, and when the content of the color developing agent is more than 50%, the color developing performance of the resultant colored image-forming layer may be saturated and an economical disadvantage may occur. When the sensitizing agent is employed, and when the content of the sensitizing agent is less than 5%, a satisfactory sensitizing effect on the colored image-forming layer may not be expected. Also, when the content of the sensitizing agent is more than 50% by weight, the sensitizing effect may be saturated and no further enhancement in the sensitivity of the colored image-forming layer may be expected.

Where the thermosensitive colored image-forming layer contains a conventional phenolic compound- or organic acid-containing color developing compound, the content of the conventional color-developing compound is preferably 5 to 40% by weight based on the total dry weight of the colored image-forming layer. When the sensitizing agent is contained, the content of the sensitizing agent is preferably 10 to 40% by weight based on the total dry weight of the colored image-forming layer. When the wax and the white pigments are contained, the contents of the wax and the white pigment are respectively 2 to 20% by weight and 2 to 50% by weight based on the total dry weight of the colored image-forming layer. Also, the binder is contained in a content of 5 to 20% by weight based on the total dry weight of the colored image-forming layer.

The white pigments for the thermosensitive colored image-forming layer are preferably selected from fine particulate inorganic white pigments, for example, calcium carbonate, silica, zinc oxide, titanium dioxide, aluminum hydroxide, zinc hydroxide, barium sulfate, clay, calcinated clay, talc, and surface-treated calcium carbonate and silica pigments; and fine particulate organic white pigments, for example, urea-formaldehyde resin, styrene-methacrylate copolymer, and polystyrene resin pigments.

The wax usable for the present invention may be selected from conventional waxes, for example, paraffin waxes, amide waxes, bisimide waxes and higher fatty acid metal salt waxes.

The binder usable for the present invention preferably comprises at least one member selected from water-soluble polymeric materials, for example, various polyvinyl alcohols different in molecular weight from each other, starch and derivatives thereof such as oxidized starch, cellulose derivatives such as methoxycellulose, carboxymethylcellulose, methylcellulose and ethylcellulose, sodium salt of polyacrylic acid, polyvinyl pyrrolidone, acrylic acid amide-acrylate ester copolymers, acrylic acid amide-acrylate ester-methacrylic acid terpolymers, alkali salts of styrene-maleic anhydride copolymers, polyacrylamide, sodium alginate, gelatin and casein; and latices of polyvinyl acetate, polyurethanes, styrene-butadiene copolymers, poly acrylic acid, polyacrylate esters, vinyl chloride-vinyl acetate copolymers, polybutyl methacrylate, ethylene-vinyl acetate copolymers, and styrene-butadiene-acrylic monomer copolymers.

The substrate sheet usable for the present invention may be selected from paper sheets (acid paper sheets and neutral paper sheets), coated paper sheets produced by coating paper sheets with a pigment and/or a latex, laminate paper sheets, synthetic paper sheets made from, for example, a polyolefin resin, and plastic films.

The thermosensitive recording material is produced by coating at least one surface of the substrate sheet with a coating liquid containing the above-mentioned dye precursor, color-developing agent, binder, and optionally the above-mentioned additives, and drying the coating liquid layer on the substrate sheet. The amount of the coating liquid applied to the substrate sheet is controlled so that the resultant colored image-forming layer preferably has a dry weight of 1 to 15 $g/m^2$, more preferably 2 to 10 $g/m^2$.

In the thermosensitive recording material of the present invention, the thermosensitive colored image-forming layer is optionally coated with an uppercoat layer, for example, a protective layer or a printing layer. Also, optionally, an undercoat layer comprising a pigment, preferably an oil-absorbing pigment, and a binder, is formed between the substrate sheet layer and the thermosensitive colored image-forming layer.

EXAMPLES

The present invention will be further illustrated by the following examples.

Synthesis Example 1

Synthesis of 1,3-trimethylene bis(4-(p-toluenesulfonylaminocarbonylamino)benzoate) (Compound (II))

A three-necked flask equipped with a dropping funnel, a thermometer and a reflux condenser was charged with 10.5 g of trimethylene bis(4-aminobenzoate) (trademark: CUA-4, made by IHARA CHEMICAL KOGYO K.K.), then with 200 ml of acetonitrile. The mixture was agitated to dissolve the trimethylene bis(4-aminobenzoate) in acetonitrile. To the mixture, 13.8 g of p-toluenesulfonylisocyanate, from the dropping funnel, were added dropwise at room temperature, while the reaction mixture was stirred with a magnetic stirrer. After the agitation of the reaction mixture was continued for 5 minutes, a white precipitate was generated in a large amount. Then, the reaction mixture was heated at a temperature of 70° C. for 5 hours, cooled to room temperature and filtered. White crystals were obtained in a yield of 19.5 g.

The white crystals were subjected to a DSC analysis, an NMR analysis and an IR analysis. The analysis results are as follows.

When the white crystals were subjected to DSC (differential scanning calorimeter) analysis, two endothermic peaks were appeared at 120° C. and 180° C., and thus a clear melting temperature could not be established. This phenomenon is assumed to be due to a polymorphism of the crystals.

The results of the MMR analysis (in deuterized DMSO) are shown in units of ppm below.

δ=2.14 (m, 2H), 2.40 (s, 6H), 4.36 (d, 4H), 7.40 (d, 4H), 7.45 (d, 4H), 7.85 (d, 4H), 7.87 (d, 4H)

In addition, other peaks appeared at about δ=9.20 and 10.85, which are assumed to be due to an N—H bond.

In the results of IR analysis (KBr tablet method), the characterizing absorptions are shown below.

1715 $cm^{-1}$ (assigned to carbonyl group in urea structure)

1690 $cm^{-1}$ (assigned to carbonyl group in ester structure)

1340 and 1160 $cm^{-1}$ (assigned to sulfonyl group)

The degree of purity of the crystals was measured by HPLC.

Detector: MULTI-340, made by NIPPON BUNKO K.K.

Column: Mightysil RP-18, made by KANTO KAGAKU K.K.

The measured degree of purity was 95% (254 nm).

Synthesis Example 2

Synthesis of 1,8-(3,6-dioxaoctylene) bis(4-(p-toluenesulfonylaminocarbonylamino)benzoate) (Compound (III))

The target compound was prepared by the same procedures as in Synthesis Example 1, except that 10.5 g of trimethylene bis(4-aminobenzoate) were replaced by 11.6 g of 1,8-(3,6-dioxaoctylene) bis(4-p-aminobenzoate), and the p-toluene sulfonylisocyanate was added dropwise in an amount of 14.8 g at room temperature. White crystals were obtained in an amount of 19.7 g.

The resultant crystals were subjected to the same measurements as in Synthesis Example 1.

In the DSC analysis of the white crystals, two endothermic peaks appeared at 155° C. and 181° C., and thus a clear melting temperature could not be established. It is assumed that this phenomenone is due to a polymorphism of the crystals.

The results of the MNR analysis (in heavy DMSO) are shown in units of ppm below.

δ=2.51 (s, 6H), 3.58 (s, 4H), 3.71 (t, 4H), 4.31 (t, 4H), 7.43 (d, 4H), 7.46 (d, 4H), 7.85 (d, 4H), 7.87 (d, 4H)

Other peaks which may be due to an N—H bond, appeared at about δ=9.21 and 10.89.

In the results of IR analysis (KBr tablet method), the characterizing absorptions are shown below.

1726 $cm^{-1}$ (assigned to carbonyl group in urea structure)

1673 $cm^{-1}$ (assigned to carbonyl group in ester structure)

1351 and 1156 $cm^{-1}$ (assigned to sulfonyl group)

HPLC measurement

Detector: MULTI-340, made by NIPPON BUNKO K.K.

Column: Mightysil RP-18, made by KANTO KAGAKU K.K.

The degree of purity of the crystals measured by HPLC was 97% (254 nm).

Synthesis Example 3

Synthesis of 1,9-nonamethylene bis(4-(p-toluenesulfonylaminocarbonylamino)benzoate) (Compound (IV))

(1) Synthesis of 1,9-nonamethylene bis(4-aminobenzoate)

A three-necked flask equipped with a thermometer, a reflux condenser and a dropping funnel was charged with 7.8 g of aminobenzoic acid and 120 ml of N,N-dimethylformamide. To the resultant solution, 8.0 g of anhydrous potassium carbonate were added. While the resultant mixture was agitator using a magnetic stirrer, 8.3 g of 1,9-dibromononane were added to the mixture at room temperature. After the resultant reaction dispersion was agitated at room temperature for 5 minutes, the dispersion was heated at a temperature of 130° C. for 5 hours while refluxing, and then was cooled to room temperature, and to the resultant reaction dispersion was added 300 ml of water. The mixture was vigorously agitated. White particles were precipitated. The white particles were collected by a filtration, and refined by a re-crystallization procedure. White crystals were obtained in an amount of 10.0 g.

The analysis results of the white crystals are shown below.

Melting temperature: 117° C.

NMR analysis results (in deuterized DMSO, in units of ppm)

δ=1.35 (s, 10H), 1.63 (d, 2H), 1.67 (d, 2H), 4.11 (d, 2H), 4.14 (d, 2H), 6.56 (d, 4H), 7.63 (d, 4H)

Other peaks, which were assumed to be due to an N—H bond, appeared at about δ=3.33 and 5.88.

IR analysis results (KBr tablet method) (characterizing absorptions)

1693 $cm^{-1}$ (derived from carbonyl group in ester structure)

711 $cm^{-1}$ (derived from amino group)

(2) Synthesis of 1,9-nonamethylene bis(4-(p-toluenesulfonylaminocarbonylamino)benzoate)

The target compound was produced by the same procedures as in Synthesis Example 1, except that 10.50 g of trimethylene bis(4-aminobenzoate) were replaced by 9.95 g of 1,9-nonamethylene bis(4-aminobenzoate) and p-toluenesulfonylisocyanate was added dropwise in an amount of 9.85 g at room temperature through a dropping funnel to the 1,9-nonamethylene bis(4-aminobenzoate).

White crystals were obtained in an amount of 16.2 g.

The analysis results are as follows

Melting temperature: 168° C.

NMR analysis (in heavy DMSO) results in the units of ppm

δ=1.35 (s, 10H), 1.63 (dd, 4H), 2.40 (d, 6H), 4.20 (dd, 4H), 7.41 (d, 4H), 7.46 (d, 4H), 7.84 (d, 4H), 7.86 (d, 4H)

Other peaks, which are assumed to be due to an N—H bond, appeared at about δ=9.15 and 10.83.

IR analysis (KBr tablet method) results in specific absorptions

1723 $cm^{-1}$ (assigned to carbonyl group in urea structure)

1689 $cm^{-1}$ (assigned to carbonyl group in ester structure)

1343 and 1157 $cm^{-1}$ (assigned to sulfonyl group)

Synthesis Example 4

Synthesis of Butyl 4-(p-toluenesulfonylaminocarbonylamino)benzoate (Compound (VI))

A three necked flask equipped with a dropping funnel, a thermometer and a reflux condenser was charged with 15.4 g of n-butyl 4-aminobenzoate and then with 150 ml of acetonitrile. The mixture in the flask was agitated to dissolve the n-butyl 4-aminobenzoate in acetonitrile. To the solution, 17.3 g of p-toluenesulfonylisocyanate were added dropwise through the dropping funnel at room temperature, while the resultant mixture was agitated by a magnetic stirrer.

After the agitation of the mixture was continued for 5 minutes, an exothermic reaction occurred to precipitate a large amount of white solid particles.

The resultant reaction mixture was further heated at a temperature of 70° C. for 3 hours, cooled to room temperature and filtered. White crystals were collected in an amount of 26.5 g.

The analysis results are as follows.

Melting temperature: 155° C.

NMR measurement (in deuterized DMSO) results in the units of ppm

δ=0.93 (t, 3H), 1.42 (m, 2H), 1.68 (m, 2H), 2.41 (s, 3H), 4.22 (t, 2H), 7.46 (dd, 4H), 7.85 (dd, 4H)

Other peaks, which are considered to be derived from an N—H bond, appeared at about δ=9.17.

IR measurement (KBr tablet method) results in characterizing absorptions

1720 $cm^{-1}$ (assigned to carbonyl group in urea structure)

1692 $cm^{-1}$ (assigned to carbonyl group in ester structure)

1340 and 1158 $cm^{-1}$ (assigned to sulfonyl group)

Synthesis Example 5

Synthesis of propyl 4-(p-toluenesulfonylaminocarbonylamino)benzoate

The target compound was prepared by the same procedures as in Synthesis Example 4, except that 15.4 g of n-butyl 4-aminobenzoate were replaced by 14.3 g of n-propyl 4-aminobenzoate. White crystals in an amount of 22.5 g were collected.

The analysis results of the white crystals were as follows.

Melting temperature of 172° C.

NMR analysis (in deuterized DMSO) results in the units of ppm

δ=0.96 (t, 3H), 1.71 (m, 2H), 2.41 (s, 3H), 4.16 (m, 2H), 7.42 (d, 2H), 7.47 (d, 2H), 7.85 (d, 2H), 7.87 (d, 2H)

Other peaks, which were considered to be due to an N—H bond, appeared at about δ=9.17 and 10.85.

IR measurement (KBr tablet method) results in characterizing absorptions

1720 $cm^{-1}$ (assigned to carbonyl group in urea structure)
1690 $cm^{-1}$ (assigned to carbonyl group in ester structure)
1340 and 1160 $cm^{-1}$ (assigned to sulfonyl group)

Example 1

A thermosensitive recording sheet was prepared by the following procedures.

(1) Preparation of a Pigment-coated Paper Sheet

A coating liquid was prepared by mix an aqueous dispersion of 85 parts by weight of calcined clay (trademark: ANSILEX, made by ENGELHARD CORPORATION) in 320 parts by weight of water with 40 parts by weight of an aqueous emulsion of a styrene-butadiene copolymer having a solid content of 50% by weight and 50 parts by weight of a 10% aqueous oxidized starch solution. The coating liquid was coated in a dry solid amount of 7.0 $g/m^2$ on a paper sheet having a basis weight of 48 $g/m^2$ and dried. A pigment-coated paper sheet was obtained.

(2) Preparation of a Dye Precursor Dispersion (A)

| Component | Part by weight |
|---|---|
| 3-(N,N-dibutylamino)-6-methyl-7-anilinofluoran | 20 |
| 10% aqueous polyvinyl alcohol solution | 10 |
| Water | 70 |

A mixture of the above-mentioned components was subjected to a pulverizing procedure using a sand grinder to such an extent that the average particle size of the dye precursor was 1 μm or less.

(3) Preparation of Color Developing Dispersion (B)

| Component | Part by weight |
|---|---|
| 1,3-trimethylene bis(4-(p-toluenesulfonylaminocarbonylamino) benzoate) | 20 |
| 10% aqueous polyvinyl alcohol solution | 10 |
| Water | 70 |

A mixture of the above-mentioned components were subjected to a pulverizing procedure using a sand grinder to such an extent that the average particle size of the color-developing agent was 1 μm or less.

(4) Preparation of Sensitizing Agent Dispersion (C)

| Component | Part by weight |
|---|---|
| Di-p-methylbenzyl oxalate | 20 |
| 10% aqueous polyvinyl alcohol solution | 10 |
| Water | 70 |

A mixture of the above-mentioned components was subjected to a pulverizing procedure using a sand grinder to such an extent that the average particle size of the sensitizing agent was 1 μm or less.

(5) Formation of a Thermosensitive Colored Image-forming Layer

A coating liquid for a thermosensitive colored image-forming layer was prepared by mixing 60 parts by weight of the dispersion (A), 120 parts by weight of the dispersion (B) and 120 parts by weight of the dispersion (C) with 23 parts by weight of a kaolinite pigment (trademark: HG CLAY, made by HUBER CO.), 20 parts by weight of a 25% aqueous zinc stearate dispersion, 15 parts by weight of a 30% aqueous paraffin dispersion and 120 parts by weight of a 10% aqueous polyvinyl alcohol solution, and stirring the mixture.

The coating liquid was coated on a surface of the pigment-coated paper sheet and dried to form a thermosensitive colored image-forming layer having a dry solid amount of 5.0 $g/m^2$ on the pigment-coated paper sheet.

A thermosensitive recording sheet was obtained.

(6) Super Calender Treatment

The thermosensitive recording sheet was subjected to a supper calender treatment, to form a smoothed surface with a Bekk smoothness of 800 to 1000 seconds.

(7) Tests

The smoothed thermosensitive recording sheet was subjected to the following tests.

(a) Whiteness

The whiteness of a sample of the thermosensitive recording sheet was measured by a HUNTER whiteness meter (made by TOYO SEIKI SEISAKUSHO).

(b) Color-forming test

A sample of the thermosensitive recording sheet was printed in a checkered pattern by using a dynamic thermosensitive color-forming simulator (Model: THPMD, made by OKURA DENKI K.K.) under a printing voltage of 21.7 volts at a pulse width of 1.0 ms.

The color density of the resultant colored images was measured by a Macbeth reflection color density tester (model: RD-914). The measured color density value represents a recording sensitivity of the recording sheet.

(c) Test for resistance of non-printed portion of recording sheet to color formation under high humidity condition A sample of the thermosensitive recording sheet was stored in a vessel at a temperature of 40° C. at a relative humidity of 90% for 24 hours. Then the color density of the sample was measured by the same procedure as in test (b).

(d) Plasticizer resistance test

A sample of the thermosensitive recording sheet printed at a pulse width of 1.0 ms in the same manner as in test (b) was, within 30 minutes after the printing, coated with dioctyl terephthalate, which is a typical plasticizer, was left to stand at room temperature for 3 hours and, thereafter, the plasticizer remaining on the sample was wipe-removed. The color density of the colored images retained on the sample was measured by the Macbeth reflection color density tester. The retention in color density of colored image was calculated in accordance with the following equation.

$$R(\%)=[C_1/C_0]\times 100$$

wherein R represents the color density retention of the sample, $C_0$ represents a color density of the colored images on the sample before the plasticizer test, and $C_1$ represents a color density of the colored images on the sample after the plasticizer test.

The results of the tests (a), (b), (c), and (d) are shown in Table 1.

Example 2

A thermosensitive recording sheet was produced and tested by the same procedures as in Example 1, with the following exceptions.

In the preparation of the aqueous dispersion (B) of the color-developing agent, the 1,3-trimethylene bis(4-(p-toluenesulfonylaminocarbonylamino)benzoate) in an amount of 20 parts by weight was replaced by a mixture of 10 parts by weight of butyl 4-(p-toluenesulfonylaminocarbonylamino)benzoate with 10 parts by weight of 1,3-trimethylene bis(4-(p-toluenesulfonylaminocarbonylamino)benzoate).

The test results are shown in Table 1.

Example 3

A thermosensitive recording sheet was produced and tested by the same procedures as in Example 1, with the following exceptions.

In the preparation of the aqueous dispersion (B) of the color-developing agent, the 1,3-trimethylene bis(4-(p-toluenesulfonylaminocarbonylamino)benzoate) in an amount of 20 parts by weight was replaced by 20 parts by weight of 1,8-(3,6-dioxaoctylene) bis(4-(p-toluenesulfonylaminocarbonylamino)benzoate).

The test results are shown in Table 1.

Example 4

A thermosensitive recording sheet was produced and tested by the same procedures as in Example 2, with the following exceptions.

In the preparation of the aqueous dispersion (B) of the color-developing agent, the 1,3-trimethylene bis(4-(p-toluenesulfonylaminocarbonylamino)benzoate) in the mixture was replaced by 10 parts by weight of 1,8-(3,6-dioxaoctylene) bis(4-(p-toluenesulfonylaminocarbonylamino)benzoate).

The test results are shown in Table 1.

Example 5

A thermosensitive recording sheet was produced and tested by the same procedures as in Example 2, with the following exceptions.

In the preparation of the aqueous dispersion (B) of the color-developing agent, the 1,3-trimethylene bis(4-(p-toluenesulfonylaminocarbonylamino)benzoate) in an amount of 20 parts by weight was replaced by a mixture of 20 parts by weight of 1,9-nonamethylene bis(4-(p-toluenesulfonylaminocarbonylamino)benzoate).

The test results are shown in Table 1.

Example 6

A thermosensitive recording sheet was produced and tested by the same procedures as in Example 2, with the following exceptions.

In the preparation of the aqueous dispersion (B) of the color-developing agent, the 1,3-trimethylene bis(4-(p-toluenesulfonylaminocarbonylamino)benzoate) in the mixture was replaced by 10 parts by weight of 1,9-nonamethylene bis(4-(p-toluenesulfonylaminocarbonylamino)benzoate).

The test results are shown in Table 1.

Example 7

A thermosensitive recording sheet was produced and tested by the same procedures as in Example 3, with the following exceptions.

In the preparation of the aqueous dispersion (B) of the color-developing agent, the 10% aqueous polyvinyl alcohol solution was replaced by an aqueous solution of 10% by weight of hydroxypropylmethylcellulose (trademark: METOLOSE 60SH03, made by SHINETSU KAGAKUKOGYO K.K.).

The test results are shown in Table 1.

Comparative Example 1

A thermosensitive recording sheet was produced and tested by the same procedures as in Example 1, with the following exceptions.

In the preparation of the aqueous dispersion (B) of the color-developing agent, the 1,3-trimethylene bis(4-(p-toluenesulfonylaminocarbonylamino)benzoate) in an amount of 20 parts by weight was replaced by 20 parts by weight of 2,2-bis(4-(p-hydroxyphenyl)propane, namely bisphenol A.

The test results are shown in Table 1.

TABLE 1

| | Item | | | |
|---|---|---|---|---|
| Example No. | Color density of colored images formed at 1.0 ms (test (b)) | Whiteness (test (a)) | Color density (test (c)) | Plasticizer resistance (test (d)) (%) |
| Example 1 | 1.30 | 83.6 | 0.06 | 86 |
| 2 | 1.32 | 83.5 | 0.06 | 80 |
| 3 | 1.33 | 83.2 | 0.06 | 90 |
| 4 | 1.33 | 83.3 | 0.06 | 82 |
| 5 | 1.31 | 83.4 | 0.06 | 88 |
| 6 | 1.32 | 83.2 | 0.06 | 81 |
| 7 | 1.33 | 83.8 | 0.06 | 90 |
| Comparative Example 1 | 1.33 | 77.9 | 0.11 | 18 |

Table 1 clearly shows that the thermosensitive recording sheets of the present invention exhibited a high whiteness and a high resistance of the non-printed portions of the recording sheet to color formation under high humidity, high temperature conditions, and a high color-developing performance, and the resultant colored images exhibited a high resistance to the plasticizer.

Also it was confirmed that the 1,3-trimethylene bis(4-(p-toluenesulfonylaminocarbonylamino)benzoate) of the formula (II), the 1,8-(3,6-dioxaoctylene) bis(4-(p-toluenesulfonylaminocarbonylanimo)benzoate) of the formula (III) and 1,9-nonamethylene bis(4-(p-toluenesulfonylaminocarbonylamino)benzoate) of the formula (IV) are new compounds having chemical structures clearly established by the various analytical methods and exhibit, as a color-developing agent, a high color-developing performance and are useful in practice.

The thermosensitive recording materials of the present invention include, in the thermosensitive colored image-forming layer thereof, an aromatic compound of the formula (I), as a color developing agent, and exhibit a high whiteness and a high resistance of the non-printed portions thereof to color-formation under high temperature, high humidity conditions. Also the colored images formed in the colored image-forming layer exhibit a high color density and an excellent retention in storage. Thus the thermosensitive recording material of the present invention is very useful in practice.

Also, the compounds of the general formula (I) exhibit an excellent color developing performance for the dye precursors.

What is claimed is:

1. A bis(arylsulfonylaminocarbonylaminobenzoate) compound of the formula (I):

(I)

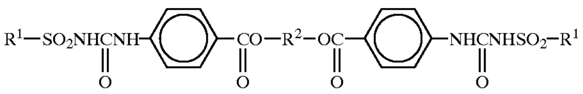

wherein $R^1$ represents a member selected from the group consisting of unsubstituted aryl groups and substituted aryl groups with at least one substituent selected from the group consisting of a methyl group and a chlorine atom, and $R^2$ represents a divalent organic group having 3 or more carbon atoms.

2. The bis(arylsulfonylaminocarbonylaminobenzoate) compound as claimed in claim 1, wherein in the formula (I), the divalent organic group represented by $R^2$ is selected from the group consisting of $-(CH_2)_m-$ group and $-(CH_2CH_2O)_n-CH_2CH_2-$ group wherein m represents an integer of 3 to 30 and n represents an integer of 1 to 20.

3. The bis(arylsulfonylaminocarbonylaminobenzoate) compound as claimed in claim 1, selected from the group consisting of:

1,3-trimethylene bis(4-(p-toluenesulfonylaminocarbonylamino)benzoate) of the formula (II):

(II)

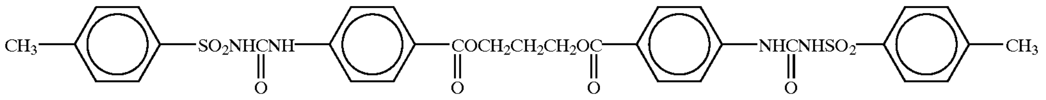

1,8-(3,6-dioxaoctylene)bis(4-(p-toluenesulfonylaminocarbonylamino)benzoate) of the formula (III):

(III)

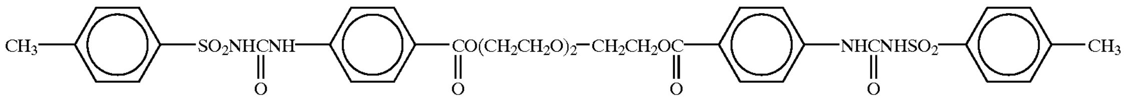

and 1.9-nonamethylene bis(4-(p-toluenesulfonylaminocarbonylamino)benzoate) of the formula (IV):

(IV)

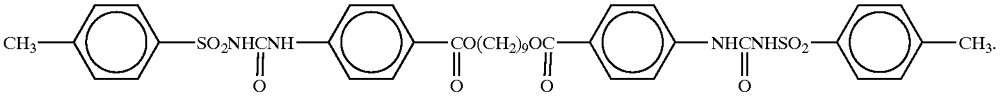

* * * * *